(12) United States Patent
Hwang et al.

(10) Patent No.: US 10,979,696 B2
(45) Date of Patent: *Apr. 13, 2021

(54) METHOD AND APPARATUS FOR DETERMINING INTERPUPILLARY DISTANCE (IPD)

(71) Applicant: SAMSUNG ELECTRONICS CO., LTD., Suwon-si (KR)

(72) Inventors: Hyoseok Hwang, Suwon-si (KR); Dongwoo Kang, Seoul (KR); Byong Min Kang, Yongin-si (KR); Juyong Park, Seongnam-si (KR); Dong Kyung Nam, Yongin-si (KR)

(73) Assignee: SAMSUNG ELECTRONICS CO., LTD., Suwon-si (KR)

(*) Notice: Subject to any disclaimer, the term of this patent is extended or adjusted under 35 U.S.C. 154(b) by 0 days.

This patent is subject to a terminal disclaimer.

(21) Appl. No.: 16/684,736

(22) Filed: Nov. 15, 2019

(65) Prior Publication Data

US 2020/0084433 A1 Mar. 12, 2020

Related U.S. Application Data

(63) Continuation of application No. 15/627,594, filed on Jun. 20, 2017, now Pat. No. 10,506,219.

(30) Foreign Application Priority Data

Nov. 29, 2016 (KR) .................. 10-2016-0160183

(51) Int. Cl.
*G06K 9/00* (2006.01)
*H04N 13/327* (2018.01)
(Continued)

(52) U.S. Cl.
CPC ......... *H04N 13/327* (2018.05); *A61B 3/0025* (2013.01); *A61B 3/111* (2013.01);
(Continued)

(58) Field of Classification Search
CPC .............. G06K 9/00604; G06K 9/0061; G06T 2207/30201
See application file for complete search history.

(56) References Cited

U.S. PATENT DOCUMENTS 6,697,761 B2 2/2004 Akatsuka et al.
6,962,289 B2 11/2005 Vatan et al.
(Continued)

FOREIGN PATENT DOCUMENTS

JP 3992045 B2 10/2007
KR 10-1348723 B1 1/2014
(Continued)

OTHER PUBLICATIONS

Normal Interpupillary distances—in population, Hamid Fesharaki et al., Journal of optahlmic and vision research, 2012, pp. 231-234 (Year: 2012).*

(Continued)

*Primary Examiner* — Jayesh A Patel
(74) *Attorney, Agent, or Firm* — Sughrue Mion, PLLC

(57) ABSTRACT

A method and apparatus for determining an interpupillary distance (IPD) are provided. To determine an IPD of a user, three-dimensional (3D) images for candidate IPDs may be generated, and user feedback on the 3D images may be received. A final IPD may be determined based on the user feedback.

15 Claims, 15 Drawing Sheets

(51) Int. Cl.
*H04N 13/383* (2018.01)
*A61B 3/11* (2006.01)
*A61B 3/00* (2006.01)

(52) U.S. Cl.
CPC ....... *G06K 9/0061* (2013.01); *G06K 9/00604* (2013.01); *H04N 13/383* (2018.05); *G06T 2207/30201* (2013.01)

(56) References Cited

U.S. PATENT DOCUMENTS

| | | | |
|---|---|---|---|
| 7,315,415 B2 | 1/2008 | Pai et al. | |
| 8,094,927 B2* | 1/2012 | Jin | G06T 15/10 382/154 |
| 9,025,252 B2 | 5/2015 | Lewis et al. | |
| 9,081,181 B2* | 7/2015 | Lee | G02B 27/017 |
| 9,213,163 B2* | 12/2015 | Lewis | G02B 27/017 |
| 9,291,834 B2 | 3/2016 | Silva et al. | |
| 9,648,313 B1* | 5/2017 | Henry | G02B 27/0101 |
| 10,506,219 B2* | 12/2019 | Hwang | A61B 3/111 |
| 2003/0063105 A1* | 4/2003 | Agnew | G06T 11/60 345/660 |
| 2007/0189742 A1* | 8/2007 | Knaan | A61B 3/113 396/18 |
| 2008/0088529 A1* | 4/2008 | Tang | G02B 27/0172 345/8 |
| 2010/0110374 A1* | 5/2010 | Raguin | G06K 9/0061 351/206 |
| 2010/0271461 A1* | 10/2010 | Takizuka | H04N 13/194 348/43 |
| 2011/0298795 A1* | 12/2011 | Van Der Heijden | H04N 13/327 345/419 |
| 2012/0200495 A1* | 8/2012 | Johansson | H04N 13/279 345/156 |
| 2013/0076884 A1* | 3/2013 | Choukroun | G06T 7/62 348/78 |
| 2013/0136302 A1* | 5/2013 | Nam | G06K 9/00281 382/103 |
| 2014/0274391 A1* | 9/2014 | Stafford | H04N 13/327 463/32 |
| 2014/0285641 A1* | 9/2014 | Kato | A61B 5/0496 348/54 |
| 2014/0293021 A1* | 10/2014 | Yu | H04N 13/383 348/51 |
| 2015/0065952 A1* | 3/2015 | Pacheco | A61B 34/30 604/95.01 |
| 2015/0146169 A1* | 5/2015 | Ye | A61B 3/0083 351/204 |
| 2015/0264336 A1* | 9/2015 | Catt | H04N 13/296 348/47 |
| 2015/0286069 A1* | 10/2015 | Allione | G01M 11/02 351/159.75 |
| 2015/0306330 A1* | 10/2015 | Richard | A61B 5/6803 348/77 |
| 2015/0350637 A1* | 12/2015 | Noguchi | H04N 13/383 348/54 |
| 2015/0358539 A1* | 12/2015 | Catt | G06T 5/006 348/38 |
| 2016/0057412 A1* | 2/2016 | Lee | H04N 13/366 348/51 |
| 2016/0065953 A1* | 3/2016 | Heo | H04N 13/368 348/54 |
| 2016/0147410 A1* | 5/2016 | Nam | G06F 3/017 345/158 |
| 2016/0156896 A1* | 6/2016 | Heo | H04N 13/371 345/156 |
| 2016/0156902 A1* | 6/2016 | Lee | H04N 13/117 348/51 |
| 2016/0225153 A1* | 8/2016 | Kim | G06T 7/64 |
| 2017/0200285 A1* | 7/2017 | Hwang | A61B 3/10 |

FOREIGN PATENT DOCUMENTS

| | | |
|---|---|---|
| KR | 10-2014-0100289 A | 8/2014 |
| KR | 10-2016-0044918 A | 4/2016 |
| KR | 10-2016-0065686 A | 6/2016 |
| KR | 10-2017-0083225 A | 7/2017 |

OTHER PUBLICATIONS

Visual fatigue—observations, Kazuhiko Ukai et al., Elsevier Science Direct, 2008, pp. 106-116 (Year: 2008).*

Sotiris Malassiotis et al., "Pose and Illumination Compensation for 3D Face Recognition", Informatics and Telematics Institute, Thessaloniki, Greece, 2004 International Conference on Image Processing, Singapore, Oct. 24-27, 2004.

Kyung-Moo Huh et al., "3D Display Method for Moving Viewers", The Magazine of the IEEK, Jul. 2000, (9 Pages Total).

Sanghoon Kim et al.,"Eye Localization based on Multi-Scale Gabor Feature Vector Model", The Journal of the Korea Contents Association, Jan. 2007, (10 Pages Total).

* cited by examiner

FIG. 7
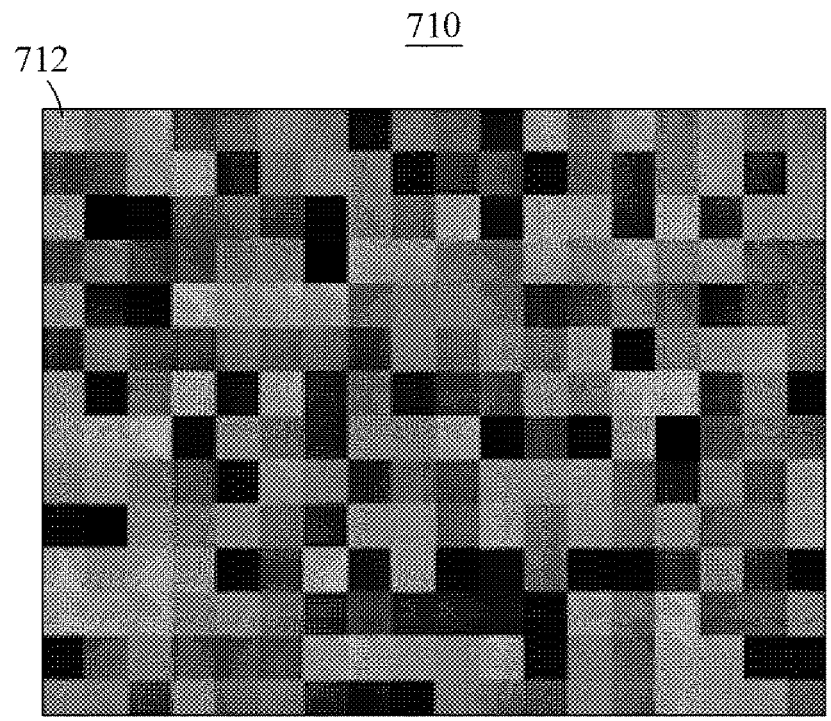
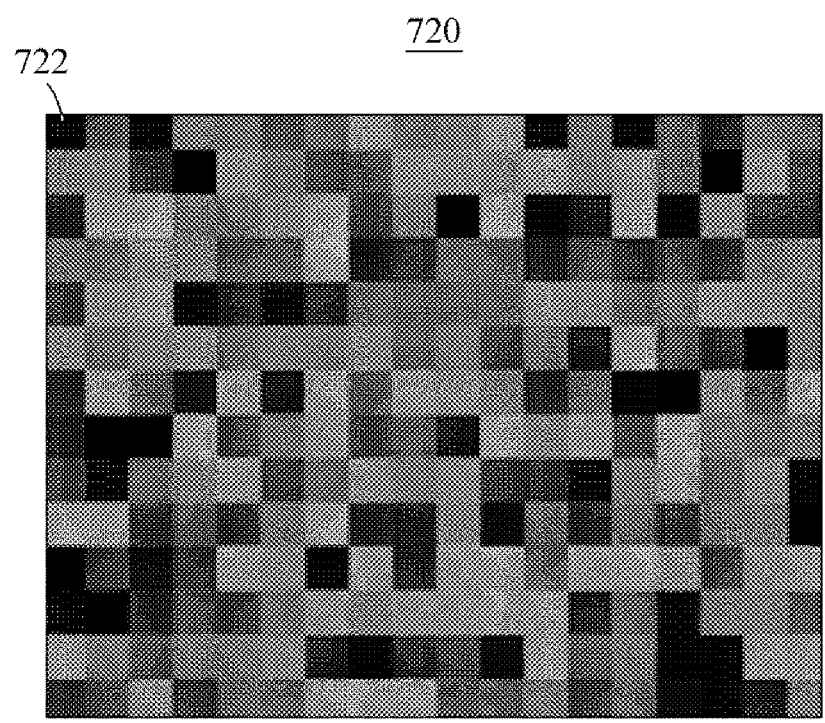

FIG. 8
810
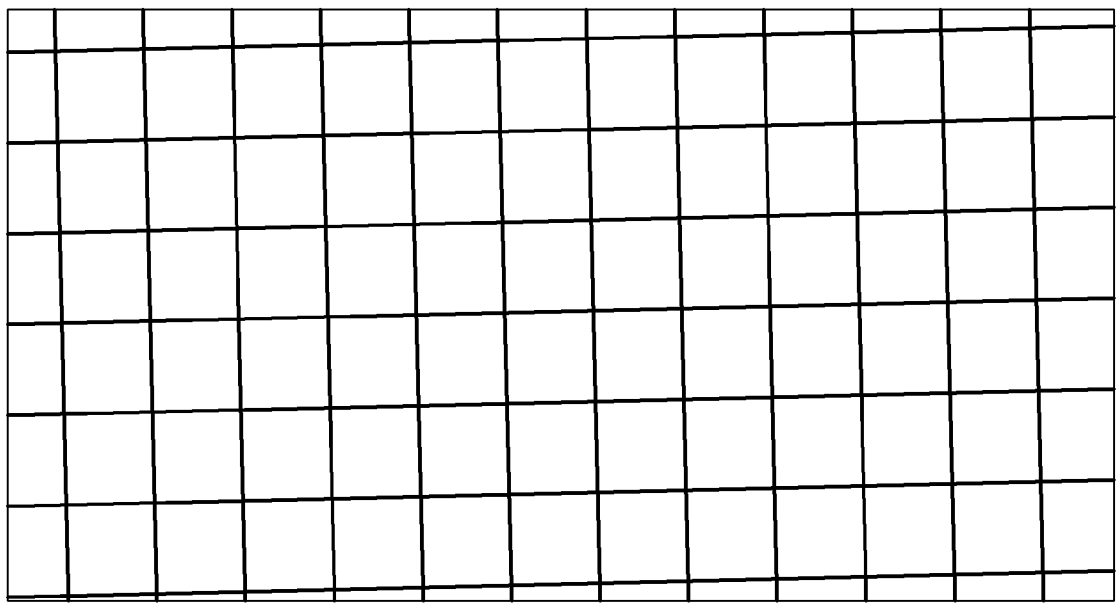
820
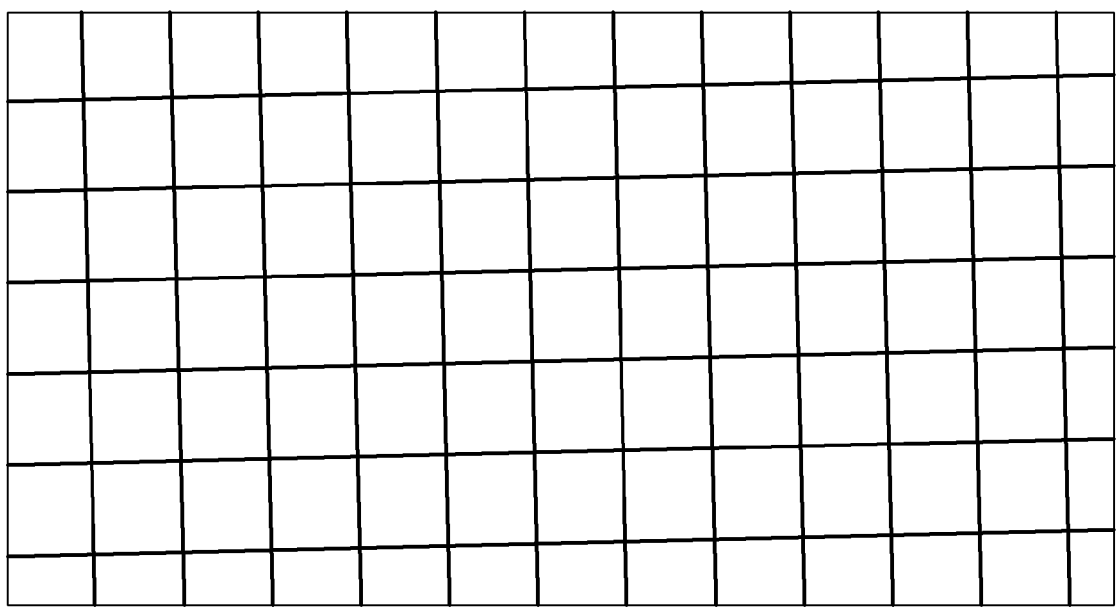

METHOD AND APPARATUS FOR DETERMINING INTERPUPILLARY DISTANCE (IPD)

CROSS-REFERENCE TO RELATED APPLICATION

This is a continuation application of U.S. patent application Ser. No. 15/627,594, filed Jun. 20, 2017, in the U.S. Patent and Trademark Office, which claims priority from Korean Patent Application No. 10-2016-0160183, filed on Nov. 29, 2016, in the Korean Intellectual Property Office, the disclosures of which are incorporated by reference herein in its entirety.

BACKGROUND

1. Field

Methods and apparatuses consistent with exemplary embodiments relate to a method and apparatus for determining an interpupillary distance (IPD), and more particularly, to a method and apparatus for determining an IPD based on user feedback on three-dimensional (3D) images generated based on candidate IPDs.

2. Description of the Related Art

An interpupillary distance (IPD) refers to a distance between pupils of human eyes. An IPD is measured in advance to perform a medical procedure of eyes in an ophthalmic clinic. To measure an IPD, a measuring device, such as a ruler, may be used. When a measuring device is used, an IPD may vary based on a user of the measuring device.

Recently, research is being conducted on a method of effectively transferring a three-dimensional (3D) image to a user as a technical field for displaying a 3D image is growing. To effectively transfer a 3D image, an image must be provided to each of a left eye and a right eye of a user. When an axis of an optical device is not aligned with an axis of a gaze of a user, the user may experience dizziness.

SUMMARY

Exemplary embodiments may address at least the above problems and/or disadvantages and other disadvantages not described above. Also, the exemplary embodiments are not required to overcome the disadvantages described above, and an exemplary embodiment may not overcome any of the problems described above.

According to an aspect of an exemplary embodiment, there is provided a method of determining an interpupillary distance (IPD), the method including generating test three-dimensional (3D) images for each of one or more candidate IPDs calculated in advance, based on the candidate IPDs and eye coordinates of eyes in a user image acquired by capturing a user, outputting the generated test 3D images, receiving feedback that relates to the output test 3D images from the user, and determining a final IPD of the user based on the received feedback.

The method may further include detecting the eye coordinates in the user image based on the user image.

The candidate IPDs may be calculated based on a standard IPD and a scale value.

The generating of the test 3D images may include calculating 3D positions of the eyes for each of the candidate IPDs based on the eye coordinates, and generating test 3D images for each of the calculated 3D positions.

The calculating of the 3D positions may include calculating the 3D positions for each of the candidate IPDs based on the eye coordinates and a normal vector acquired from the user image.

The generating of the test 3D images may include generating a first two-dimensional (2D) image for either a left eye or a right eye, the first 2D image including pixels each having a random intensity value, and generating a second 2D image that has a pattern which is complementary to a pattern of the first 2D image.

The outputting of the test 3D images may include merging the test 3D images into a single composite test image, and outputting the composite test image.

The determining of the final IPD may include receiving one or more feedback 3D images among the output test 3D images from the user, determining whether a number of times feedback is received exceeds a preset number, updating the candidate IPDs based on IPDs of the feedback 3D images when the number of times feedback is received does not exceed the preset number, and determining a final IPD based on the IPDs of the feedback 3D images when the number of times feedback is received exceeds the preset number. The generating of the test 3D images may include generating test 3D images for each of the updated candidate IPDs.

The updating of the candidate IPDs may include adjusting at least one of a standard IPD or a scale value based on the IPDs of the feedback 3D images, and updating the candidate IPDs based on at least one of the adjusted standard IPD or the adjusted scale value.

The adjusting of at least one of the standard IPD or the scale value may include calculating an average value of the IPDs of the feedback 3D images, and adjusting the standard IPD based on the average value.

The adjusting of at least one of the standard IPD or the scale value may include determining a weight of each of the IPDs of the feedback 3D images based on an order in which the feedback 3D images are selected, and adjusting the standard IPD based on the weight and the IPDs of the feedback 3D images.

The feedback 3D images may include relatively bright images selected by the user from the output test 3D images.

The method may further include determining the user based on the user image, and associating the final IPD with the determined user when the final IPD is determined. The determining of the user may include, when an IPD is associated with the determined user, determining the associated IPD as the final IPD.

According to another aspect of an exemplary embodiment, there is provided an apparatus for determining an IPD, the apparatus including a memory configured to store a program to determine an IPD of a user, and a processor configured to execute the program, wherein the program is executed to perform generating test 3D images for each of one or more candidate IPDs calculated in advance, based on the candidate IPDs and eye coordinates of eyes in a user image acquired by capturing the user, outputting the generated test 3D images, receiving feedback on the output test 3D images from the user, and determining a final IPD of the user based on the feedback.

The apparatus may further include a camera configured to generate the user image.

The apparatus may further include a display configured to output the test 3D images.

The apparatus may further include a user interface configured to receive the feedback.

BRIEF DESCRIPTION OF THE DRAWINGS

The above and other aspects of exemplary embodiments will become apparent and more readily appreciated from the following detailed description of certain exemplary embodiments, taken in conjunction with the accompanying drawings of which:

FIG. 7 is a diagram illustrating 2D images with complementary patterns, according to an exemplary embodiment;

FIG. 8 is a diagram illustrating 2D images with 3D stereo patterns, according to an exemplary embodiment;

DETAILED DESCRIPTION

Figure 1:
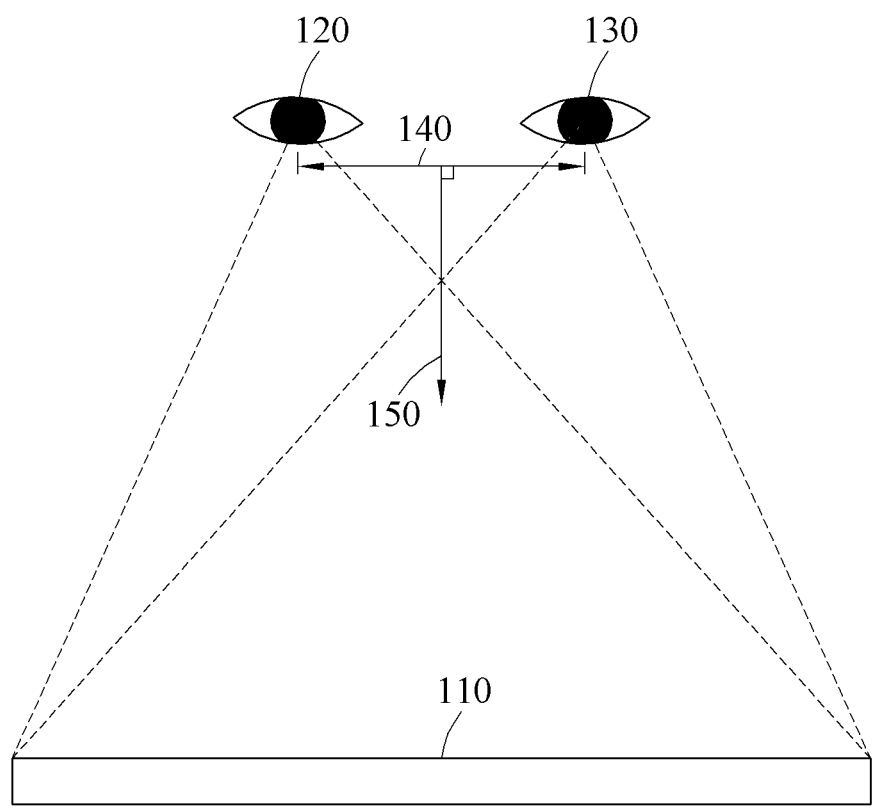
FIG. 1 is a diagram illustrating an interpupillary distance (IPD) used in a three-dimensional (3D) display, according to an exemplary embodiment.

Hereinafter, some exemplary embodiments will be described in detail with reference to the accompanying drawings. The scope of the present disclosure, however, should not be construed as limited to the exemplary embodiments set forth herein. Like reference numerals in the drawings refer to like elements throughout the present disclosure.

Various modifications may be made to the exemplary embodiments. However, it should be understood that these exemplary embodiments are not construed as limited to the illustrated forms and include all changes, equivalents or alternatives within the idea and the technical scope of the present disclosure.

The terminology used herein is for the purpose of describing particular exemplary embodiments only and is not intended to be limiting of the present inventive concep. As used herein, the singular forms "a," "an" and "the" are intended to include the plural forms as well, unless the context clearly indicates otherwise. It will be further understood that the terms "include" and/or "have," when used in this specification, specify the presence of stated features, integers, steps, operations, elements, components or combinations thereof, but do not preclude the presence or addition of one or more other features, integers, steps, operations, elements, components, and/or groups thereof.

Unless otherwise defined, all terms including technical and scientific terms used herein have the same meaning as commonly understood by one of ordinary skill in the art to which these exemplary embodiments belong. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

Regarding the reference numerals assigned to the elements in the drawings, it should be noted that the same elements will be designated by the same reference numerals, wherever possible, even though they are shown in different drawings. Also, in the description of exemplary embodiments, detailed description of well-known related structures or functions will be omitted when it is deemed that such description could cause ambiguous interpretation of the present disclosure.

FIG. 1 is a diagram illustrating an interpupillary distance (IPD) used in a three-dimensional (3D) display, according to an exemplary embodiment.

In a method of providing a 3D image, a single 3D image may be generated by rendering a left eye image and a right eye image. A display 110 may provide a right eye image and a left eye image to a right eye 120 and a left eye 130 of a user, respectively, based on a physical configuration. The physical configuration may include a lenticular lens and a parallax barrier.

To properly provide a 3D image to a user, 3D positions of eyes of the user may need to be accurately determined. To determine the 3D positions, a normal vector 150 may be used. A normal vector 150 may be a vector that vertically bisects a straight line connecting the right eye 120 and the left eye 130. The normal vector 150 may correspond to a direction of a face of the user.

Also, to determine the 3D positions, a distance between the right eye 120 and the left eye 130 may need to be accurately determined. For example, a distance 140 between a pupil of the right eye 120 and a pupil of the left eye 130 may need to be determined. The distance 140 may be referred to as an interpupillary distance (hereinafter "IPD") 140.

Figure 2:
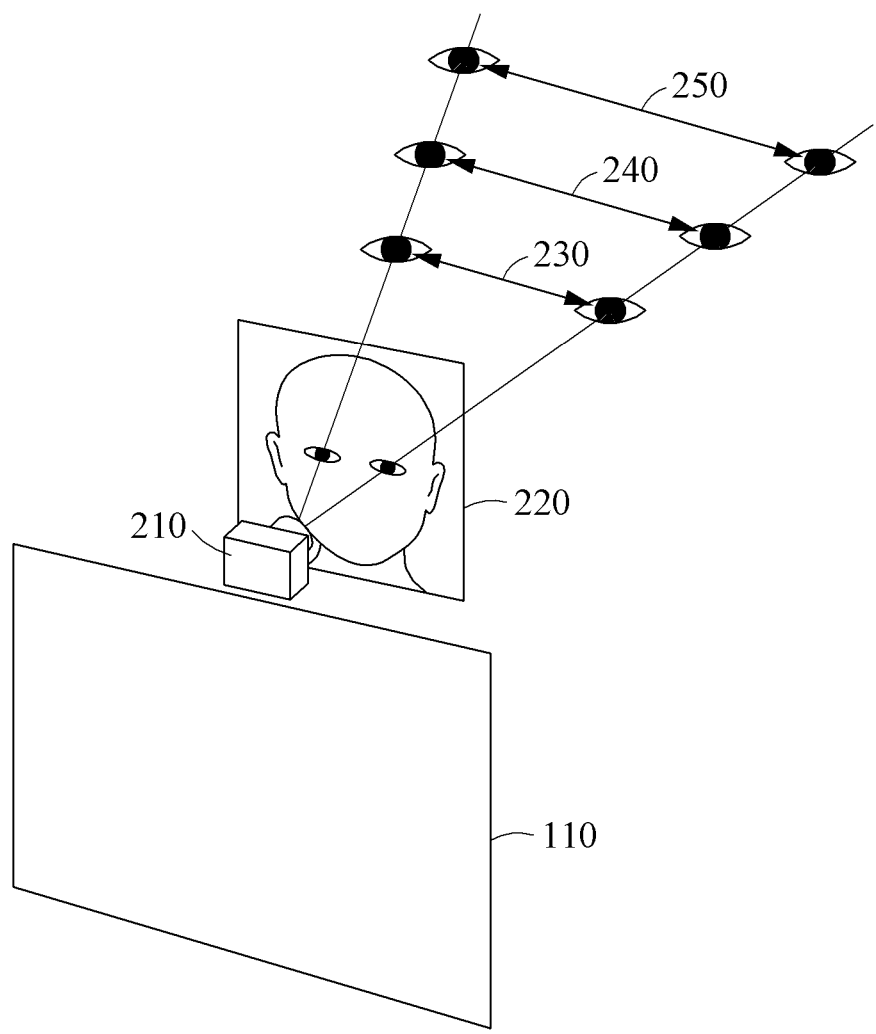
FIG. 2 is a diagram illustrating a user image and candidate IPDs, according to an exemplary embodiment.

FIG. 2 is a diagram illustrating a user image and candidate IPDs, according to an exemplary embodiment.

To determine an IPD of a user, a user image acquired by capturing the user may be used. A camera 210 may generate a user image 220 by capturing a user. An apparatus (hereinafter, referred to as an "IPD determination apparatus") for determining an IPD may detect pupil coordinates of pupils of both eyes in the user image 220 by analyzing the user image 220. The IPD determination apparatus may calculate candidate 3D positions of the pupils based on the detected pupil coordinates. The candidate 3D positions may be disposed on straight lines connecting the camera 210 and the pupils in the user image 220. For example, positions of the pupils in the user image 220 may be calculated based on an intrinsic parameter.

When a normal vector for a pupil is acquired and when an IPD is known, an accurate 3D position of the pupil may be determined. Straight lines 230, 240 and 250 that connects the pupils by the normal vector may be parallel to each other, and a straight line with a length that corresponds to the IPD among the straight lines 230, 240 and 250 may be determined as a straight line that connects the pupils at accurate positions. Thus, to determine 3D positions of the pupils, the pupil coordinates in the user image 220, the normal vector and the IPD may be used.

A method of determining an IPD will be further described with reference to FIGS. 3 through 16 below.

Figure 3:
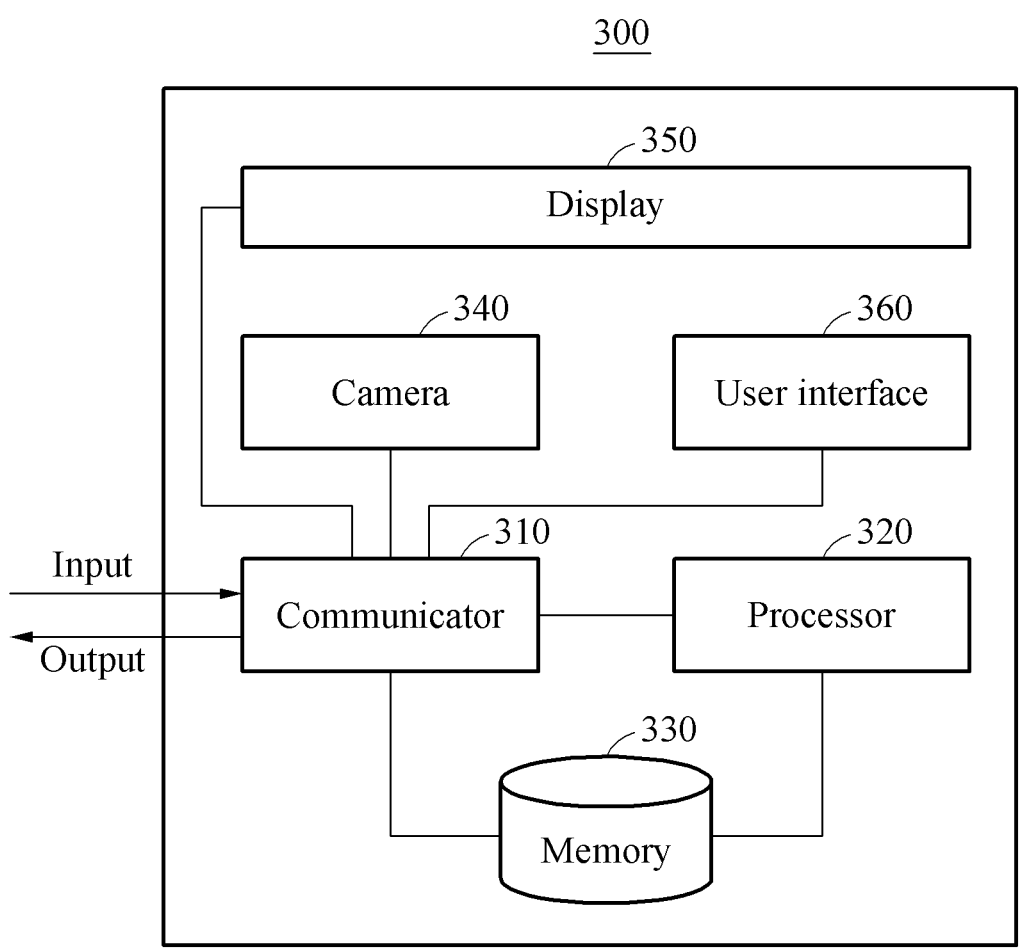
FIG. 3 is a diagram illustrating a configuration of an apparatus for determining an IPD, according to an exemplary embodiment.

FIG. 3 is a diagram illustrating a configuration of an IPD determination apparatus 300, according to an exemplary embodiment.

Referring to FIG. 3, the IPD determination apparatus 300 includes a communicator 310, a processor 320, a memory 330, a camera 340, a display 350 and a user interface 360. For example, the communicator 310, the processor 320 and the memory 330 may be implemented as a system-on-chip (SOC), however, there is no limitation thereto.

The communicator 310 may be connected to the processor 320, the memory 330, the camera 340, the display 350 and the user interface 360, and may transmit and receive data. Also, the communicator 310 may be connected to an external device, and may transmit and receive data.

The communicator 310 may be implemented as a circuitry in the IPD determination apparatus 300. In an example, the communicator 310 may include an internal bus and an external bus. In another example, the communicator 310 may be an element configured to connect the IPD determination apparatus 300 to an external device. The communicator 310 may be, for example, an interface. The communicator 310 may receive data from the external device and may transmit data to the processor 320 and the memory 330.

The processor 320 may process data received by the communicator 310 and data stored in the memory 330. The term "processor," as used herein, may be a hardware-implemented data processing device having a circuit that is physically structured to execute desired operations. For example, the desired operations may include code or instructions included in a program. The hardware-implemented data processing device may include, but is not limited to, for example, any of a microprocessor, a central processing unit (CPU), a processor core, a multi-core processor, a multiprocessor, an application-specific integrated circuit (ASIC), and a field-programmable gate array (FPGA).

The processor 320 may execute a computer-readable code (for example, software) stored in a memory (for example, the memory 330), and execute instructions caused by the processor 320.

The memory 330 may store data received by the communicator 310 and data processed by the processor 320. For example, the memory 330 may store a program. The stored program may be coded to determine an IPD and may include a set of syntax which is executable by the processor 320.

The memory 330 may include, for example, any of at least one volatile memory, a nonvolatile memory, a random access memory (RAM), a flash memory, a hard disk drive and an optical disc drive.

The memory 330 may store an instruction set (for example, software) to operate the IPD determination apparatus 300. The instruction set to operate the IPD determination apparatus 300 may be executed by the processor 320.

The camera 340 may generate an image by capturing a scene. For example, the camera 340 may generate a user image by capturing a user.

The display 350 may output an image generated by the processor 320.

The user interface 360 may receive a user input from a user and may provide an output to the user. In an example, the user interface 360 may receive a touch input from a user who is using a touch panel. In another example, the user interface 360 may receive a user input who is using a mouse and a keyboard.

The communicator 310, the processor 320, the memory 330, the camera 340, the display 350 and the user interface 360 will be further described with reference to FIGS. 4 through 16.

Figure 4:
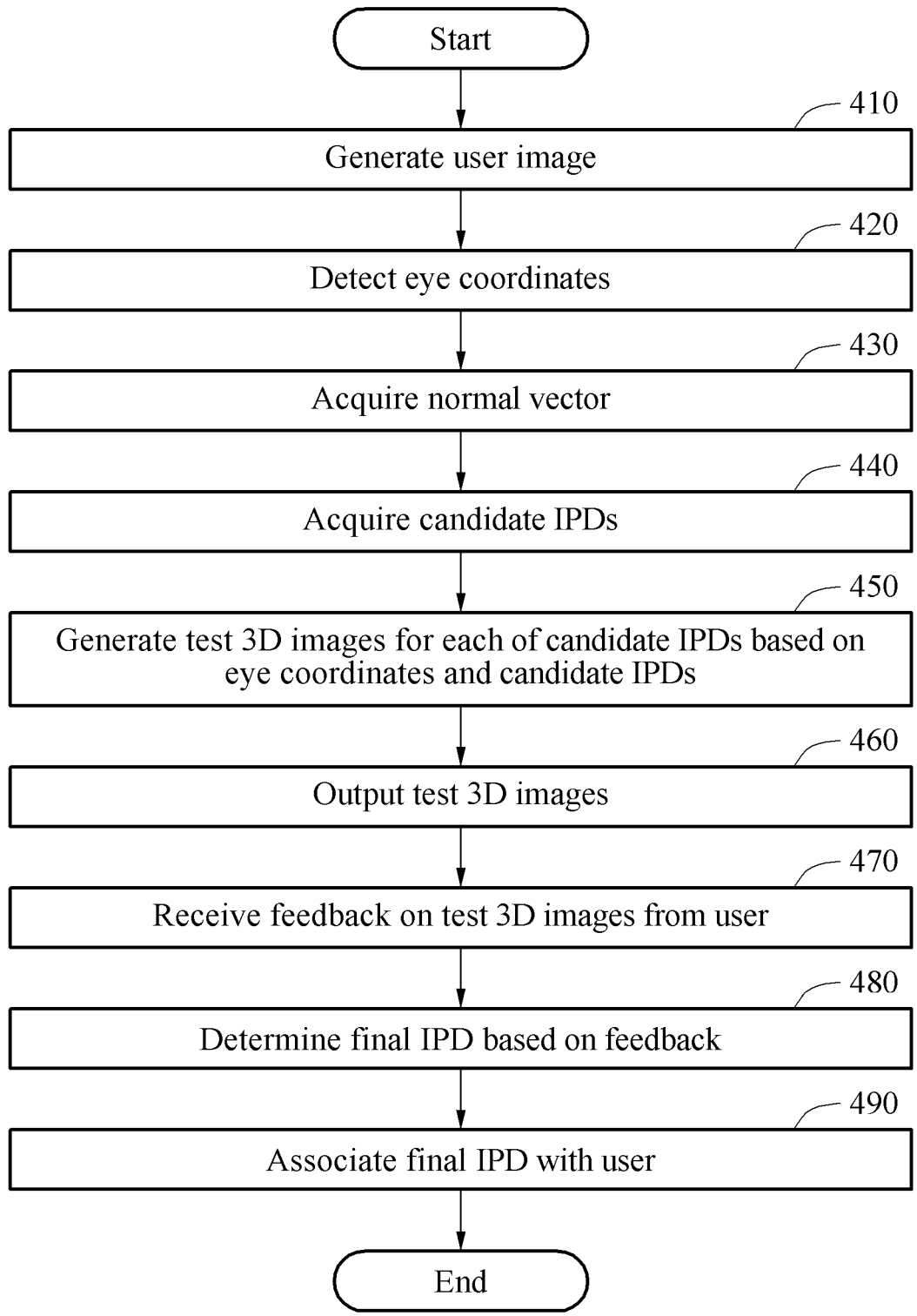
FIG. 4 is a flowchart illustrating a method of determining an IPD, according to an exemplary embodiment.

FIG. 4 is a flowchart illustrating a method of determining an IPD, according to an exemplary embodiment.

Referring to FIG. 4, in operation 410, the camera 340 generates a user image by capturing a user.

In operation 420, the processor 320 detects eye coordinates of both eyes in the user image based on the user image. The processor 320 may detect coordinates of pupils of the eyes. For example, the processor 320 may detect, as pupil coordinates, centermost coordinates from among detected coordinates of a pupil of a single eye.

In operation 430, the processor 320 acquires a normal vector for pupils of the eyes. For example, the processor 320 may calculate the normal vector based on the user image.

In operation 440, the processor 320 acquires one or more candidate IPDs calculated in advance. The processor 320 may calculate the candidate IPDs in advance before operation 410 is performed.

The processor 320 may calculate one or more candidate IPDs by using Equation 1 shown below. In Equation 1, when candidate IPDs are calculated, k may be equal to "(n+1)/2," μ may denote a standard IPD, and ε may denote a scale value. In Equation 1, n is a natural number that is greater than or equal to "1."

$$\text{Candidate IPD}(n) = \mu - \varepsilon \times (n-k) \qquad \text{[Equation 1]}$$

For example, when n is set to "9," when the standard IPD μ is set to 65 millimeters (mm) and when the scale value ε is set to "4," candidate IPDs may be calculated as 49 mm, 53 mm, 57 mm, 61 mm, 65 mm, 69 mm, 73 mm, 77 mm and 81 mm. The calculated candidate IPDs may be referred to as a "test set." Candidate IPDs calculated in advance may be referred to as a "first test set," and the first test set may have a set index of "1." A margin of "0.5" may be set for the first test set. The margin may be a rate of pixels provided for a single eye through a parallax barrier. When the margin increases, a range of an eye position to be covered may increase, however, a sharpness of a provided image may decrease.

The calculated candidate IPDs may be stored in the memory 330, and the processor 320 may load the calculated candidate IPDs from the memory 330.

In operation 450, the processor 320 generates test 3D images for each of the candidate IPDs based on the candidate IPDs and the eye coordinates. For example, when nine candidate IPDs are provided, nine test 3D images respectively corresponding to the nine candidate IPDs may be generated. To generate a test 3D image, a normal vector may be used. A method of generating a test 3D image will be further described below with reference to FIGS. 5, 6, 7, and 8.

In operation 460, the processor 320 outputs the test 3D images by using the display 350. A method of outputting test 3D images will be further described below with reference to FIGS. 9, 10, and 11.

In operation 470, the processor 320 receives user feedback via the user interface 360. The user feedback may be a selection by a user of a relatively bright image from among the output test 3D images. The processor 320 may receive feedback 3D images among the test 3D images via the user interface 360 from the user. For example, the user may select, as a feedback 3D image, one or more relatively bright test 3D images from the output test 3D images.

In operation 480, the processor 320 determines a final IPD based on the received feedback. The final IPD may be used to generate a 3D image of content. A method of determining a final IPD will be further described below with reference to FIGS. 12, 13, 14, and 15.

Figure 5:
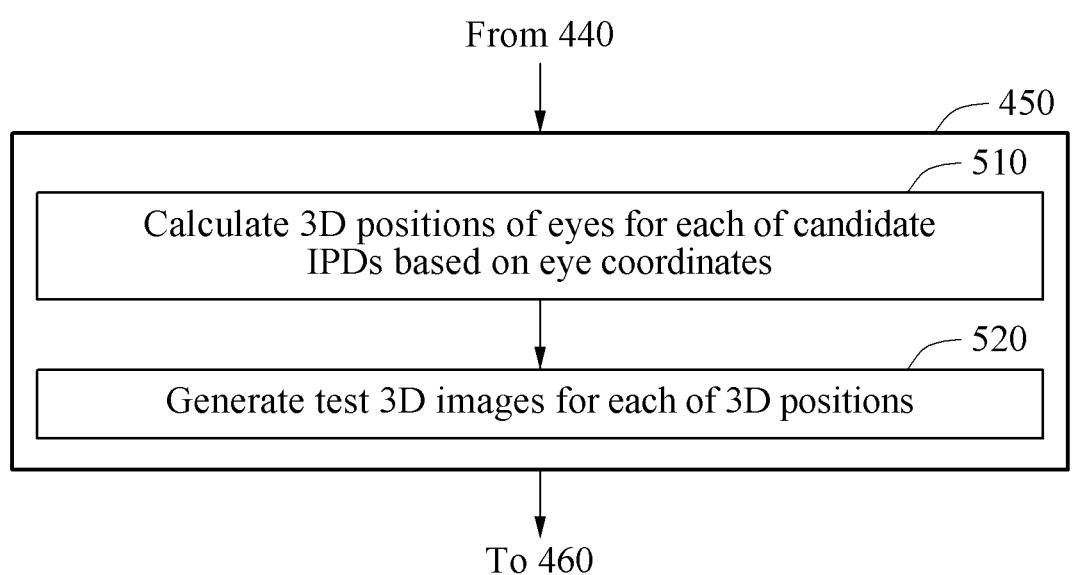
FIG. 5 is a flowchart illustrating an example of a scheme of generating test 3D images in the method of FIG. 4.

FIG. 5 is a flowchart illustrating an example of generating test 3D images in operation 450 of FIG. 4.

Referring to FIGS. 4 and 5, operation 450 may include operation 510 and operation 520.

In operation 510, the processor 320 calculates 3D positions of the eyes (or pupils) for each of the candidate IPDs based on the eye coordinates in the user image. The processor 320 may calculate the 3D position of the eyes based on the eye coordinates, the normal vector and the candidate IPDs.

In operation 520, the processor 320 generates test 3D images for each of the 3D positions. The test 3D images may be clearly formed in the 3D positions. The test 3D images may be relatively less clearly formed in positions other than the 3D positions.

Figure 6:
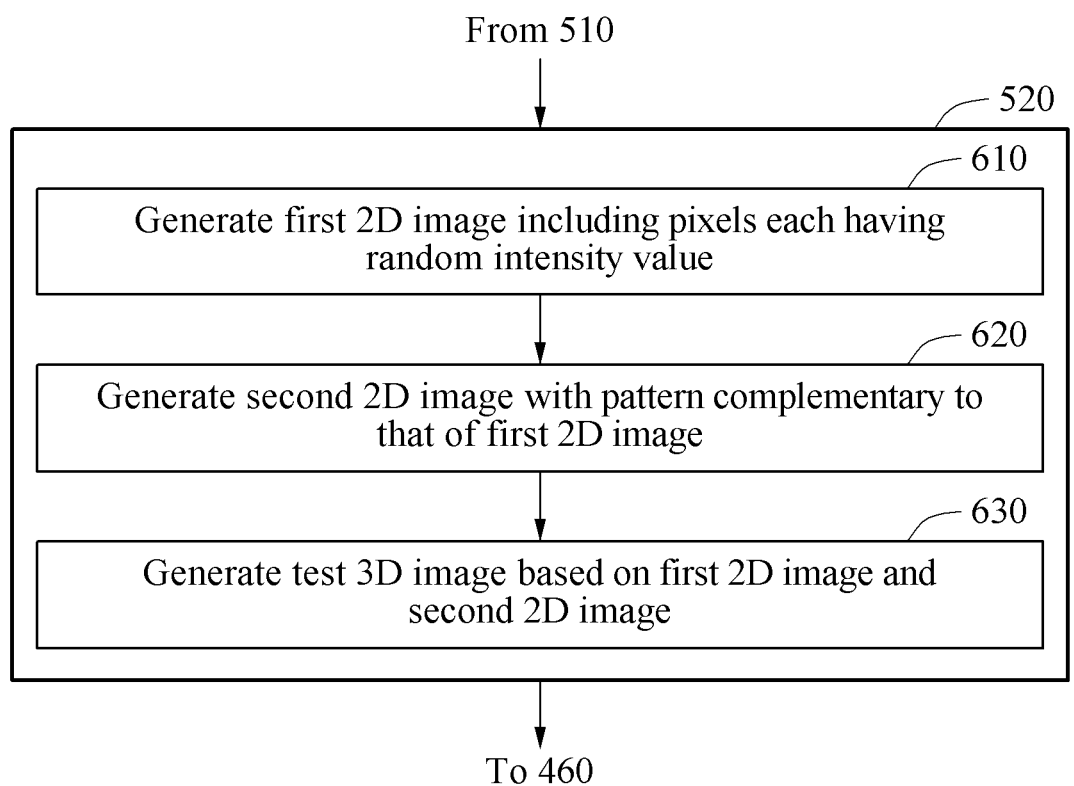
FIG. 6 is a flowchart illustrating an example of a scheme of generating test 3D images based on two-dimensional (2D) images with complementary patterns in the scheme of FIG. 5.

FIG. 6 is a flowchart illustrating an example of generating test 3D images based on 2D images with complementary patterns in operation 520 of FIG. 5.

Referring to FIGS. 5 and 6, operation 520 may include operation 610, operation 620, and operation 630.

In operation 610, the processor 320 generates a first 2D image that includes a plurality of pixels, where each pixel has a random intensity value. The first 2D image may be, for example, a 2D image for a left eye or a right eye. For example, when 8 bits are assigned to a single pixel, a random intensity value from among intensity values of "0" through "255" may be set to the pixel.

In operation 620, the processor 320 generates a second 2D image that has a pattern which is complementary to a pattern of the first 2D image. When the first 2D image is a left eye image, the second 2D image may be a right eye image. The first 2D image, and the second 2D image with the pattern complementary to that of the first 2D image will be further described below with reference to FIG. 7.

In operation 630, the processor 320 generates a test 3D image based on the first 2D image and the second 2D image. When an exact IPD is reflected, the generated test 3D image may appear to be relatively bright to the user.

FIG. 7 is a diagram illustrating 2D images with complementary patterns, according to an exemplary embodiment.

When 8 bits are assigned to a single pixel, an intensity value of a pixel 712 of a first 2D image 710 and an intensity value of a pixel 722 of a second 2D image 720 may be determined such that the intensity values up to "255." The pixels 712 and 722 may have the same coordinates. In an example, when the pixel 712 has an intensity value of "0," the intensity value of the pixel 722 may be set to "255." In another example, when the pixel 712 has an intensity value of "154," the intensity value of the pixel 722 may be set to "101."

FIG. 8 is a diagram illustrating 2D images with 3D stereo patterns, according to an exemplary embodiment.

Each of a left eye image 810 and a right eye image 820 may have a stereo pattern. When an exact IPD is reflected in a test 3D image generated based on the left eye image 810 and the right eye image 820, a user may recognize the test 3D image in 3D. When an exact IPD is not reflected in a test 3D image generated based on the left eye image 810 and the right eye image 820, the test 3D image may appear to a user partially in 2D, or may appear to the user as if patterns of the left eye image 810 and the right eye image 820 overlap.

Figure 9:
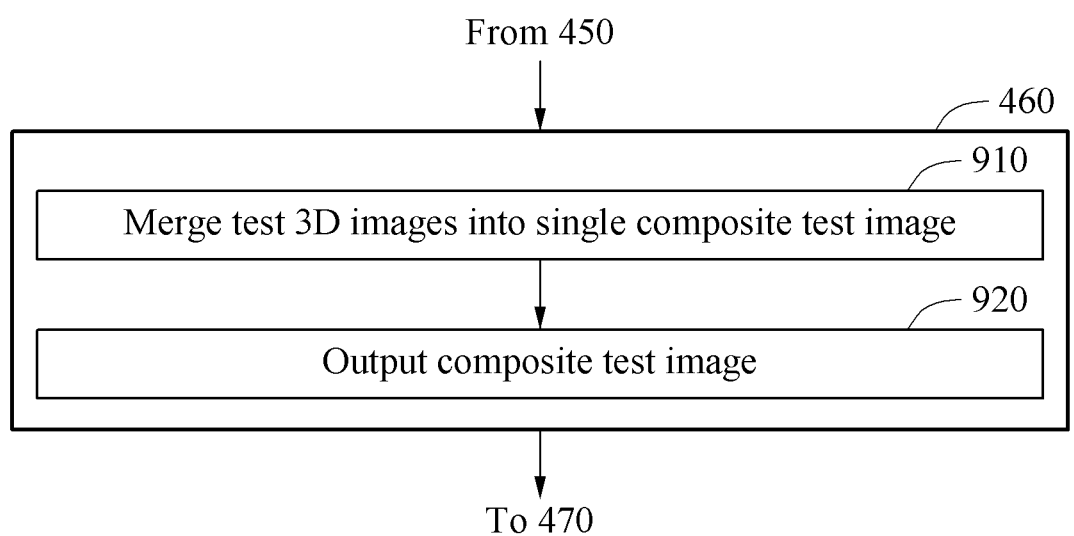
FIG. 9 is a flowchart illustrating an example of a scheme of outputting test 3D images in the method of FIG. 4.

FIG. 9 is a flowchart illustrating an example of outputting test 3D images in operation 460 of FIG. 4.

Referring to FIGS. 4 and 9, operation 460 may include operation 910 and operation 920.

In operation 910, the processor 320 merges the test 3D images generated for each of the candidate IPDs into a single composite test image. By merging one or more test 3D images into a single composite test image, the one or more test 3D images may be simultaneously output. Examples of a composite test image will be further described below with reference to FIGS. 10 and 11.

In operation 920, the processor 320 outputs the composite test image by using the display 350. When the test 3D images are simultaneously output, a user may easily compare the test 3D images. For example, the user may compare brightness between the test 3D images.

Figure 10:
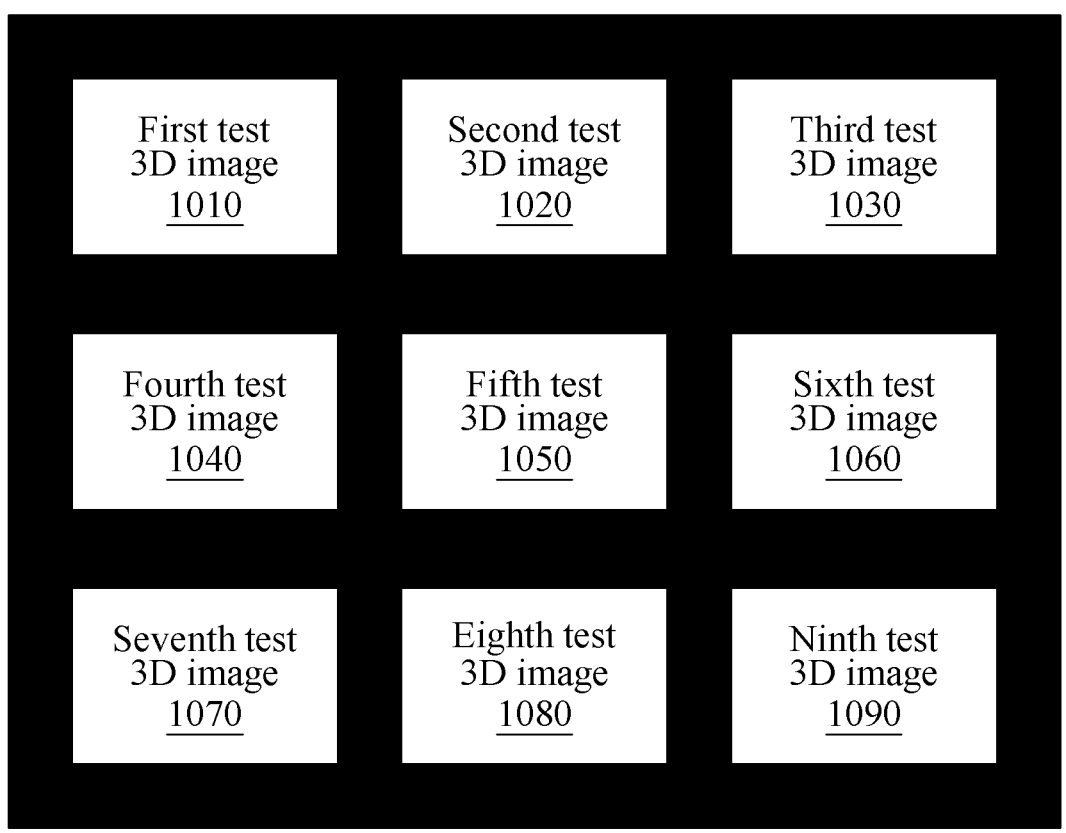
FIG. 10 is a diagram illustrating an example of a composite test image, according to an exemplary embodiment.

FIG. 10 is a diagram illustrating an example of a composite test image, according to an exemplary embodiment.

A first test 3D image 1010, a second test 3D image 1020, a third test 3D image 1030, a fourth test 3D image 1040, a fifth test 3D image 1050, a sixth test 3D image 1060, a seventh test 3D image 1070, an eighth test 3D image 1080, and a ninth test 3D image 1090 for each of candidate IPDs may be merged into a single composite test image 1000. Each of the first test 3D image 1010 through the ninth test 3D image 1090 may form a 3D image in a predicted 3D position of a pupil. In an example, a test 3D image generated for a candidate IPD predicted to be less than an exact IPD may form a 3D image ahead of an exact 3D position of a pupil. In another example, a test 3D image generated for a candidate IPD predicted to be greater than an exact IPD may form a 3D image behind an exact 3D position of a pupil.

In an example, when a test 3D image is generated based on complementary patterns and when an exact IPD is reflected in the test 3D image, the test 3D image may appear as being relatively bright to a user. The user may select one or more relatively bright test 3D images from among output test 3D images. For an accurate contrast, pixels in the composite test image 1000 other than the first test 3D image 1010 through the ninth test 3D image 1090 may have darkest pixel values.

In another example, when a test 3D image is generated based on stereo patterns and when an exact IPD is reflected in the test 3D image, a clear 3D object may be provided to a user. The user may select one or more test 3D images that show relatively clear 3D objects from among output test 3D images.

Figure 11:
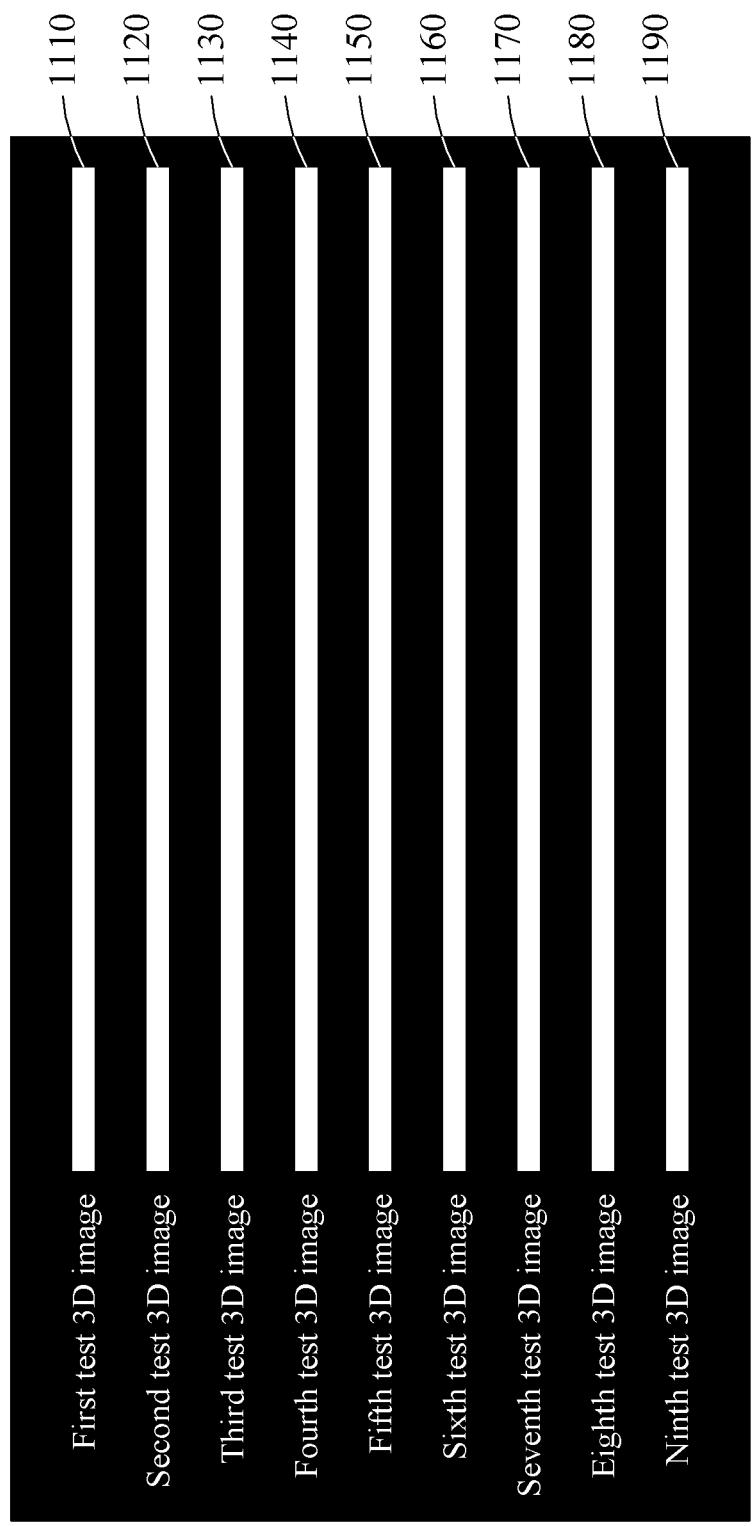
FIG. 11 is a diagram illustrating another example of a composite test image, according to an exemplary embodiment.

FIG. 11 is a diagram illustrating another example of a composite test image, according to an exemplary embodiment.

A first test 3D image 1110, a second test 3D image 1120, a third test 3D image 1130, a fourth test 3D image 1140, a fifth test 3D image 1150, a sixth test 3D image 1160, a seventh test 3D image 1170, an eighth test 3D image 1180, and a ninth test 3D image 1190 for each of candidate IPDs may be merged into a single composite test image 1100.

Each of the first test 3D image 1110 through the ninth test 3D image 1190 may be generated in a form of a bar or a strip. To predict a more precise IPD, a test 3D image may be generated in the form of a bar. For example, the first test 3D image 1010 through the ninth test 3D image 1090 of FIG. 10 may have a margin of "0.5," and the first test 3D image 1110 through the ninth test 3D image 1190 may have a margin of "0.2." When a margin value decreases, a range of a 3D position of a pupil to be covered may decrease. Accordingly, a test 3D image generated for a candidate IPD that is greatly different from an actual IPD may appear as being relatively dark to a user. When test 3D images are widely distributed in a horizontal direction, a difference in brightness between the first test 3D image 1110 through the ninth test 3D image 1190 may be shown to the user.

Figure 12:
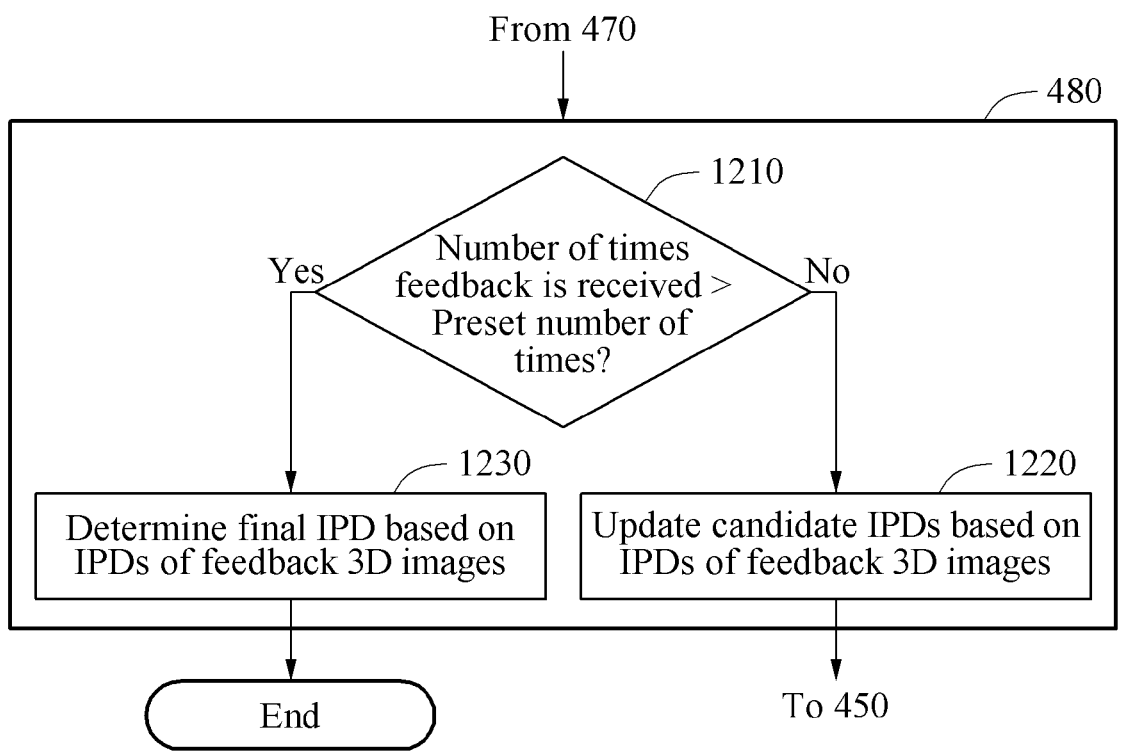
FIG. 12 is a flowchart illustrating an example of a scheme of determining a final IPD in the method of FIG. 4.

FIG. 12 is a flowchart illustrating an example of determining a final IPD in operation 480 of FIG. 4.

Referring to FIGS. 4 and 12, operation 480 may include operation 1210, operation 1220, and operation 1230.

In operation 1210, the processor 320 determines whether a number of times feedback is received exceeds a preset number. The number of times the feedback is received may correspond to a number of times test images are output. For example, a number of times operation 470 is performed may be the same as the number of times the feedback is received. When the first test set is used to generate test 3D images, the feedback may be received once. When the second test set is used to generate test 3D images, the feedback may be received twice, which will be further described below.

When the number of times the feedback is received does not exceed the preset number, operation 1220 may be performed. When the number of times the feedback is received exceeds the preset number, operation 1230 may be performed.

In operation 1220, the processor 320 updates the candidate IPDs based on IPDs of feedback 3D images selected by a user. When the candidate IPDs are updated, operations 450, 460 and 470 of FIG. 4 may be reperformed. Operations 450, 460 and 470 may be reperformed in response to updating of the candidate IPDs, and thus a more exact IPD may be determined. A method of updating candidate IPDs will be further described below with reference to FIGS. 13, 14, and 15.

When operation 1220 is performed, operation 450 may be performed. In operation 450, the processor 320 may generate test 3D images for each of the updated candidate IPDs based on the updated candidate IPDs and the eye coordinate in the user image. When operation 450 is reperformed, the updated candidate IPDs may correspond to the second test set. The second test set may have a set index of "2." A margin set for the second test set may be less than a margin set for the first test set.

When operation 450 is reperformed, operations 460 and 470 may be reperformed. Operations 460 and 470 may be performed for the second test set.

In operation 1230, the processor 320 determines a final IPD based on the IPDs of the feedback 3D images. When a number of times is set to "n" in advance and feedback 3D images for an (n+1)-th test set are received, a final IPD may be determined based on IPDs of the feedback 3D images for the (n+1)-th test set.

In an example, the processor 320 may determine an average value of the IPDs of the feedback 3D images as a final IPD. In another example, the processor 320 may set a weight of each of the IPDs of the feedback 3D images in an order in which the feedback 3D images are selected, and may determine a final IPD based on the weight and the IPDs of the feedback 3D images.

Figure 13:
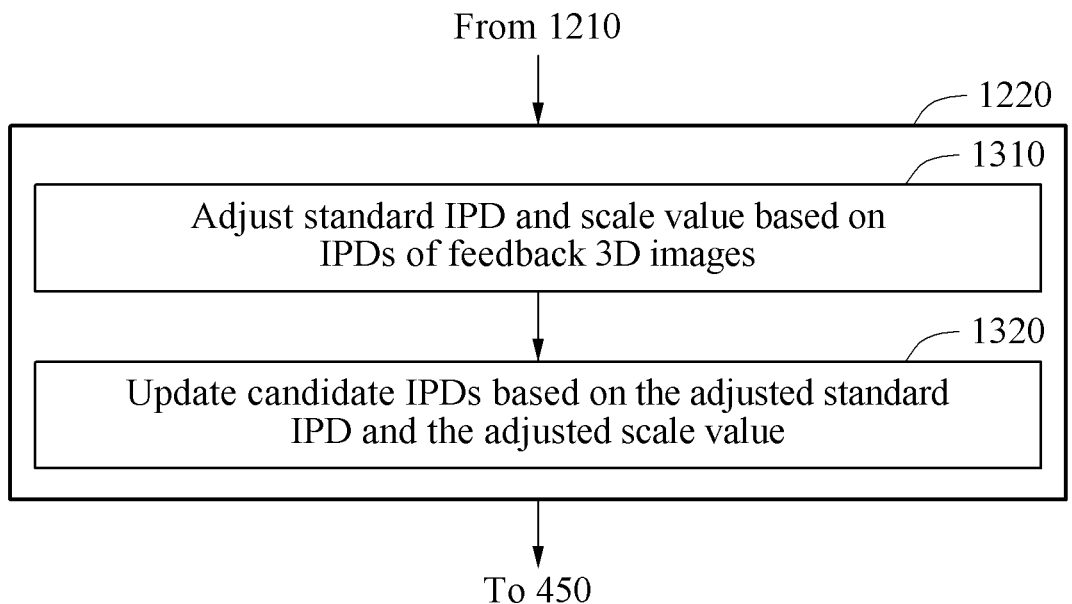
FIG. 13 is a flowchart illustrating an example of a scheme of updating candidate IPDs in the scheme of FIG. 12.

FIG. 13 is a flowchart illustrating an example of updating candidate IPDs in operation 1220 of FIG. 12.

Referring to FIGS. 12 and 13, operation 1220 may include operation 1310 and operation 1320.

In operation 1310, the processor 320 adjusts at least one from among a standard IPD and a scale value based on the IPDs of the feedback 3D images. The standard IPD and the scale value may be denoted by, for example, $\mu$ and $\varepsilon$, respectively. The scale value may be adjusted based on the number of times the feedback is received, or a number of times a test set is updated. In an example, when candidate IPDs for the first test set are updated, the scale value may be adjusted to a value of "b" that is less than a value of "a" used to generate the candidate IPDs for the first test set. In another example, when candidate IPDs for the second test set are updated, the scale value may be adjusted to a value of "c" that is less than a value of "b" used to generate the candidate IPDs for the second test set.

The processor 320 may adjust the standard IPD based on the IPDs of the feedback 3D images. A method of adjusting a standard IPD will be further described below with reference to FIGS. 14 and 15.

In operation 1320, the processor 320 updates the candidate IPDs based on the adjusted standard IPD and the adjusted scale value. For example, the processor 320 may calculate the candidate IPDs using the above-described Equation 1. When operation 1320 is performed "n" times, the updated candidate IPDs may be referred to as a (n+1)-th test set.

Figure 14:
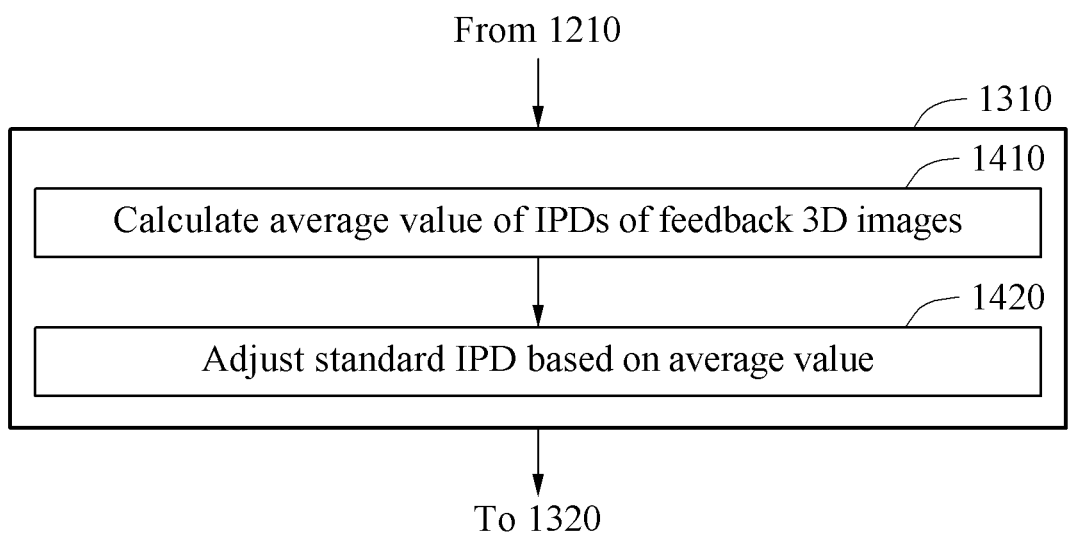
FIG. 14 is a flowchart illustrating an example of a scheme of adjusting a standard IPD in the scheme of FIG. 13.

FIG. 14 is a flowchart illustrating an example of adjusting a standard IPD in operation 1310 of FIG. 13.

Referring to FIGS. 13 and 14, operation 1310 may include operation 1410 and operation 1420.

In operation 1410, the processor 320 calculates an average value of the IPDs of the feedback 3D images.

In operation 1420, the processor 320 adjusts the standard IPD based on the calculated average value. For example, the calculated average value may be set as the standard IPD.

Figure 15:
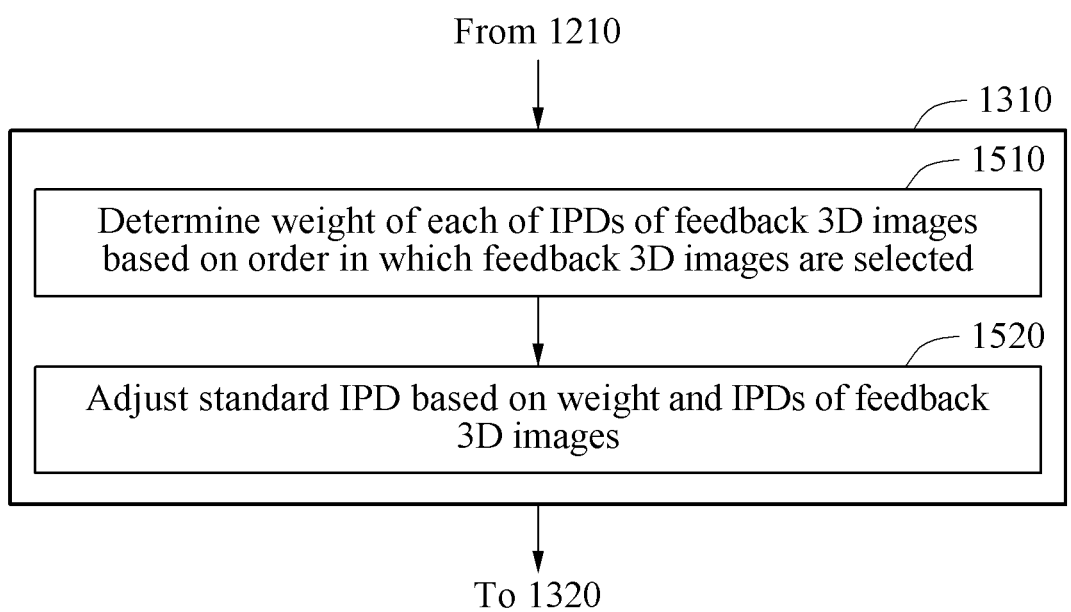
FIG. 15 is a flowchart illustrating another example of a scheme of adjusting a standard IPD in the scheme of FIG. 13.

FIG. 15 is a flowchart illustrating another example of adjusting a standard IPD in operation 1310 of FIG. 13.

Referring to FIGS. 13 and 15, operation 1310 may include operation 1510 and operation 1520.

In operation 1510, the processor 320 determines a weight of each of the IPDs of the feedback 3D images based on an order in which the feedback 3D images are selected by a user. For example, when a user selects feedback 3D images from the output test 3D images in an order that corresponds to a relative brightness of each of the test 3D images, a relatively large weight may be determined for an IPD of a feedback 3D image that is selected first.

In operation 1520, the processor 320 adjusts the standard IPD based on the determined weight and the IPDs of the feedback 3D images. For example, a weighted average value of the IPDs of the feedback 3D images may be determined as the standard IPD.

Figure 16:
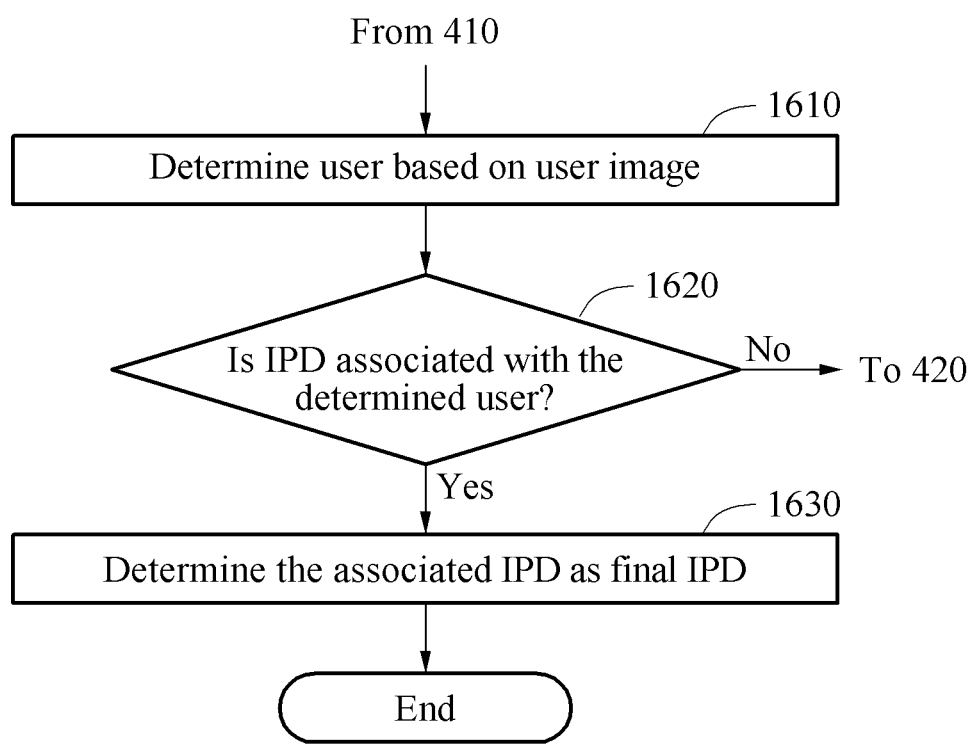
FIG. 16 is a flowchart illustrating an example of a scheme of determining a final IPD based on an IPD associated with a user, according to an exemplary embodiment.

FIG. 16 is a flowchart illustrating an example of determining a final IPD based on an IPD associated with a user, according to an exemplary embodiment.

Referring to FIGS. 4 and 16, operation 1610, operation 1620, and operation 1630 may be performed after operation 410.

In operation 1610, the processor 320 determines the user based on the user image. For example, the processor 320 may detect a face of the user based on the user image, and may determine whether the detected face has been stored in a database (DB) in advance. The processor 320 may distinguish users based on feature points of faces. When the detected face has not previously been stored in the DB, the processor 320 may generate information about a new user.

In operation 1620, the processor 320 determines whether an IPD is associated with the determined user. When the IPD is associated with the determined user, the associated IPD may be determined as a final IPD in operation 1630. When the IPD is not associated with the determined user, operation 420 of FIG. 4 may be performed to determine an IPD of the user.

The exemplary embodiments described herein may be implemented by using hardware components, software components, or a combination thereof. A processing device may be implemented by using one or more general-purpose or special purpose computers, such as, for example, a processor, a controller and an arithmetic logic unit, a digital signal processor, a microcomputer, a field programmable array, a programmable logic unit, a microprocessor or any other device capable of responding to and executing instructions in a defined manner. The processing device may run an operating system (OS) and one or more software applications that run on the OS. The processing device also may access, store, manipulate, process, and create data in response to execution of the software. For purpose of simplicity, the description of a processing device is used as singular; however, one skilled in the art will appreciate that a processing device may include multiple processing elements and multiple types of processing elements. For example, a processing device may include multiple processors or a processor and a controller. In addition, different processing configurations are possible, such as parallel processors.

The software may include a computer program, a piece of code, an instruction, or some combination thereof, to independently or collectively instruct or configure the processing device to operate as desired. Software and data may be embodied permanently or temporarily in any type of machine, component, physical or virtual equipment, computer storage medium or device, or in a propagated signal wave that is capable of providing instructions or data to or being interpreted by the processing device. The software also may be distributed over network coupled computer systems so that the software is stored and executed in a distributed fashion. The software and data may be stored by one or more non-transitory computer readable recording mediums.

The method according to the above-described exemplary embodiments may be recorded in non-transitory computer-readable media including program instructions to implement various operations which may be performed by a computer. The media may also include, alone or in combination with the program instructions, data files, data structures, and the like. The program instructions recorded on the media may be those specially designed and constructed for the purposes of the exemplary embodiments, or they may be of the well-known kind and available to those having skill in the computer software arts. Examples of non-transitory computer-readable media include magnetic media such as hard disks, floppy disks, and magnetic tape; optical media such as compact disk-read-only memory (CD ROM) discs and digital versatile disks (DVDs); magneto-optical media such as optical discs; and hardware devices that are specially configured to store and perform program instructions, such as read-only memory (ROM), random access memory (RAM), flash memory, and the like. Examples of program instructions include both machine code, such as code produced by a compiler, and files containing higher level code that may be executed by the computer using an interpreter. The described hardware devices may be configured to act as one or more software modules in order to perform the operations of the above-described exemplary embodiments, or vice versa.

While the present disclosure includes exemplary embodiments, it will be apparent to one of ordinary skill in the art that various changes in form and details may be made in these exemplary embodiments without departing from the spirit and scope of the claims and their equivalents. The exemplary embodiments described herein are to be considered in a descriptive sense only, and not for purposes of limitation. Descriptions of features or aspects in each exemplary embodiment are to be considered as being applicable to similar features or aspects in other exemplary embodiments. Suitable results may be achieved if the described techniques are performed in a different order, and/or if components in a described system, architecture, device, or circuit are combined in a different manner and/or replaced or supplemented by other components or their equivalents. Therefore, the scope of the present disclosure is defined not by the detailed description, but by the claims and their equivalents, and all variations within the scope of the claims and their equivalents are to be construed as being included in the present disclosure.

What is claimed is:

1. A method for determining an interpupillary distance (IPD), the method comprising:
   detecting eye coordinates of eyes of a user in a user image;
   acquiring a normal vector of a line connecting pupils of the eyes, from the user image;
   generating test three-dimensional (3D) images respectively for candidate IPDs, based on the candidate IPDs, the detected eye coordinates and the acquired normal vector;
   merging the generated test 3D images into a single composite test image;
   outputting the single composite test image into which the test 3D images are merged;
   receiving, from the user, a selection of an image among the test 3D images merged into the output single composite test image; and
   obtaining a final IPD of the user, based on one of the candidate IPDs corresponding to the selected image.

2. The method of claim 1, wherein the candidate IPDs are obtained based on a standard IPD and a scale value.

3. The method of claim 1, wherein the generating the test 3D images comprises:
   obtaining 3D positions of the eyes for each of the candidate IPDs, based on the candidate IPDs, the detected eye coordinates and the acquired normal vector; and
   generating the test 3D images respectively for the obtained 3D positions of the eyes for each of the candidate IPDs.

4. The method of claim 1, wherein the generating the test 3D images comprises:
   generating a first two-dimensional (2D) image for one from among a left eye and a right eye, the first 2D image comprising pixels, wherein each of the pixels has a random intensity value;
   generating a second 2D image having a pattern that is complementary to a pattern of the generated first 2D image; and generating one of the test 3D images, based on the generated first 2D image and the generated second 2D image.

5. The method of claim 1, wherein the obtaining the final IPD comprises:
identifying whether a number of times feedback is received from the user exceeds a preset number;
based on the number of times feedback is received being identified to not exceed the preset number, updating the candidate IPDs, based on the one of the candidate IPDs corresponding to the selected image; and
based on the number of times feedback is received being identified to exceed the preset number, obtaining the final IPD, based on the one of the candidate IPDs corresponding to the selected image, and
wherein the generating the test 3D images comprises generating the test 3D images respectively for the updated candidate IPDs, based on the updated candidate IPDs, the detected eye coordinates and the acquired normal vector.

6. The method of claim 5, wherein the updating the candidate IPDs comprises:
adjusting either one or both of a standard IPD and a scale value, based on the one of the candidate IPDs corresponding to the selected image; and
updating the candidate IPDs, based on either one or both the adjusted standard IPD and the adjusted scale value.

7. The method of claim 6, wherein the adjusting either one or both of the standard IPD and the scale value comprises:
obtaining an average value of one or more of the candidate IPDs corresponding to one or more of the test 3D images that are selected by the user, from the output single composite test image; and
adjusting the standard IPD, based on the obtained average value.

8. The method of claim 6, wherein the adjusting either one or both of the standard IPD and the scale value comprises:
obtaining a weight of each of one or more the candidate IPDs corresponding to one or more of the test 3D images that are selected by the user, from the output single composite test image, based on an order in which the one or more of the test 3D images are selected; and
adjusting the standard IPD, based on the obtained weight each of the one or more the candidate IPDs and the one or more of the candidate IPDs.

9. The method of claim 1, wherein the selected image is a relatively bright image among the test 3D images merged into the output single composite test image.

10. The method of claim 1, further comprising:
determining the user, based on the user image;
identifying whether the determined user is associated with an associated IPD;
based on the determined user being identified to be associated with the associated IPD, obtaining the associated IPD as the final IPD,
wherein the obtaining the final IPD comprises, based on the determined user being identified to not be associated with the associated IPD, obtaining the final IPD, based on the one of the candidate IPDs corresponding to the selected image; and
associating the obtained final IPD with the determined user.

11. A non-transitory computer-readable storage medium storing a program for causing a processor to perform the method of claim 1.

12. An apparatus for determining an interpupillary distance (IPD), the apparatus comprising:
a memory configured to store a program; and
a processor configured to execute the program to at least:
detect eye coordinates of eyes of a user in a user image;
acquire a normal vector of a line connecting pupils of the eyes, from the user image;
generate test three-dimensional (3D) image images respectively for candidate IPDs, based on the candidate IPDs, the detected eye coordinates and the acquired normal vector;
merge the generated test 3D images into a single composite test image;
control to output the single composite image into which the test 3D images are merged;
receive, from the user, a selection of an image among the test 3D images merged into the output single composite test image; and
obtain a final IPD of the user, based on one of the candidate IPDs corresponding to the selected image.

13. The apparatus of claim 12, further comprising a camera configured to generate the user image.

14. The apparatus of claim 12, further comprising a display configured to output the single composite image into which the test 3D images are merged.

15. The apparatus of claim 12, wherein the selected image is a relatively bright image among the test 3D images merged into the output single composite test image.

* * * * *